United States Patent [19]

Neu et al.

[11] Patent Number: 4,502,993

[45] Date of Patent: Mar. 5, 1985

[54] PROCESS FOR THE PREPARATION OF UNSATURATED ALIPHATIC CARBOXYLIC ACIDS

[75] Inventors: Hermann Neu, Neu-Isenburg; Günter Roscher, Kelkheim, both of Fed. Rep. of Germany

[73] Assignee: Hoechst Aktiengesellschaft, Frankfurt am Main, Fed. Rep. of Germany

[21] Appl. No.: 379,781

[22] Filed: May 19, 1982

[30] Foreign Application Priority Data

May 21, 1981 [DE] Fed. Rep. of Germany ....... 3120244

[51] Int. Cl.$^3$ .......................... C11C 1/04; C07C 51/00
[52] U.S. Cl. .................................... 260/415; 260/413; 562/518; 562/598; 562/601; 560/185
[58] Field of Search ........................... 260/415, 413 N; 560/185; 562/601, 518, 598

[56] References Cited

U.S. PATENT DOCUMENTS 3,021,365 2/1962 Fernholz et al. ................... 562/601
3,960,939 6/1976 Sekiyama et al. .............. 260/526 N Primary Examiner—Thomas A. Waltz
Attorney, Agent, or Firm—Curtis, Morris & Safford

[57] ABSTRACT

The invention relates to a process for the preparation of unsaturated aliphatic carboxylic acids by thermal cracking of the polymeric intermediate product ("polyester") which is formed in the catalytic reaction of aldehydes or ketones with ketene. The reaction mixture containing polyester is heated with water, and the polyester is then isolated and subjected to cracking. Or the polyester is first isolated and then heated with water and finally subjected to cracking. In both cases the temperature when the mixture is heated with water is the same as the boiling point, or is less than 40° C. below the boiling point, of the aqueous mixture.

8 Claims, No Drawings

PROCESS FOR THE PREPARATION OF UNSATURATED ALIPHATIC CARBOXYLIC ACIDS

The invention relates to a process for the preparation of unsaturated aliphatic carboxylic acids by thermal cracking of the polymeric intermediate product (described in the following text as "polyester") formed in the catalytic reaction of aldehydes or ketones with ketene. A process of this type is described, for example, in U.S. Pat. No. 3,021,365.

Catalysts which are suitable for the reaction to form the polyester are those of the Friedel-Crafts type, such as, for example, boron fluoride, aluminum chloride and zinc chloride, and also divalent metals, such as zinc, cadmium, mercury, nickel, cobalt and iron, in the form of their carboxylates. Depending on the aldehyde or ketone (described in the following text as "carbonyl compound") employed, the reaction temperature is 20°–60° C. It is advantageous to carry out the reaction in an inert solvent, such as, for example, toluene, or to react only part of the carbonyl compound, so that the excess acts as a solvent. Before the polyester is processed further, the solvent and the unreacted carbonyl compound must be removed by distillation.

The thermal cracking of the polyester is preferably carried out at temperatures of 150°–250° C., in particular at 170°–200° C., in the presence of catalytic quantities of alkali metal hydroxides or alkali metal salts having a basic reaction or secondary or tertiary amines. In general, the carboxylic acid which has been formed is removed simultaneously by distillation. If the desired unsaturated carboxylic acid is solid under normal conditions, it is advantageous to carry out the thermal cracking of the polyester and the subsequent simultaneous distillation of the acid in a high-boiling inert solvent.

It is possible to prepare in this way, for example, unsaturated aliphatic carboxylic acids having 4 to 16 C atoms (mono-unsaturated or poly-unsaturated) from the corresponding carbonyl compounds. In particular, the following unsaturated aliphatic carboxylic acids can be prepared from the carbonyl compounds indicated in each case by reacting the latter with ketene to give the corresponding polyester and subjecting this to thermal cracking: hexenoic acid from butyraldehyde, ethylhexenoic acid from ethylbutyraldehyde, ethyloctenoic acid from ethylhexanal, i-undecenoic acid from i-nonylaldehyde, heptenoic acid from valeraldehyde, hexadecenoic acid from myristaldehyde, pentadienoic acid from acrolein, hexadienoic acid from crotonaldehyde, dimethylacrylic acid from acetone and methylpentenoic acid from methyl ethyl ketone. The process is particularly suitable for the preparation of hexenoic acid, ethylhexenoic acid, i-undecenoic acid and hexadienoic acid.

Besides the unsaturated acids, higher-boiling liquid products which have no acidic properties are also formed in the thermal cracking of the polyester. These byproducts can reduce the yield of unsaturated carboxylic acid considerably and can lead to discoloration.

It has been found, surprisingly, that by heating the polyester with water before the thermal cracking reaction, the formation of these high-boilers is repressed, the yield of unsaturated acid is increased and the quality of the latter is substantially improved.

The process, according to the invention, for the preparation of unsaturated aliphatic carboxylic acids by the thermal cracking of the polyester formed in the condensation reaction of carbonyl compounds with ketene, if appropriate in the presence of a solvent, comprises heating the reaction mixture containing the polyester, or the polyester isolated therefrom, after adding water, to a temperature which is the same as the boiling point or below the boiling point by less than 40° C., before subjecting the polyester, if appropriate after it has been isolated, to cracking. It is preferable to carry out the process at the boiling point or below the boiling point by less than 20° C., but particularly at the boiling point itself.

The temperature is thus approximately 60°–100° C., preferably approximately 80°–100° C. and particularly approximately 100° C., if the process is carried out under normal pressure. The heating with water can, however, also be carried out under pressure or under vacuum, in which case the boiling point and the position of the 40 degree temperature range are shifted correspondingly. However, it is preferable to carry out the process under normal pressure. In addition, it is preferable to carry out the process under reflux.

The quantity of water added can be varied within wide limits. In general, it is sufficient to add 5–20% by weight of water, relative to the polyester employed, but even larger quantities can be added without affecting the effect described. The duration of the treatment with water depends on the polyester employed, as a rule it is between 30 and 60 minutes. A longer duration of heating has no adverse effect on the yield, but it does not provide any further advantages, either. The heating in the presence of water can be carried out either before or after removing, by distillation, the low-boilers, the unreacted carbonyl compound and, if appropriate, the solvent. It is preferably carried out beforehand.

A particularly advantageous procedure is to add the water and the catalyst for cracking the polyester to the reaction mixture containing the polyester after the reaction of the carbonyl compound with ketene, and to boil the mixture under reflux under normal pressure. Low-boilers, unreacted carbonyl compound, water and solvent are then removed by distillation. The bottom product, which is essentially composed of polyester, is then brought to the temperature of 150°–200° C. which is required for the cracking reaction. The unsaturated carboxylic acid is distilled off under vacuum at a rate corresponding to its rate of formation. Even without the use of a column, the unsaturated acid is obtained in such a high state of purity, by simple distillation, that a further purification operation, e.g. by repeated distillation, is unnecessary. Without heating with water in accordance with the invention, such a quality of acid cannot be achieved so easily, since even distillation through a column at a high reflux ratio always gives products which are still slightly yellow in color, apart from the fact that this step reduces the yield considerably.

The following examples illustrate the invention.

COMPARISON EXAMPLE 1

(a) Ketene was passed into a mixture of 250 g of butyraldehyde, 250 g of toluene and 7.5 g of zinc isobutyrate at 30°–40° C. until the increase in weight corresponded to 80–90% conversion of the aldehyde employed. After the reaction, 5 g of dioctadecylamine were added to the mixture containing polyester.

(b) The low-boilers, the unreacted butyraldehyde and the toluene were then removed by distillation. The polyester was then cracked by applying a vacuum of 25 mbar and increasing the bottom temperature to 170°–200° C., and the hexenoic acid was distilled off continuously. 205 g of hexenoic acid (boiling point 117° C./25) were obtained, corresponding to a yield of 61.0%, relative to butyraldehyde which had reacted. The absorption of light at 415 nm in a layer of thickness 1 cm was 89%, compared with water.

EXAMPLE 1

(a) The procedure followed was as in part (a) of Comparison Example 1.

(b) 40 g of water were added to the mixture and the latter was heated to the boil under reflux for 30 minutes. The low-boilers, the unreacted butyraldehyde, the water and the toluene were then removed by distillation. The polyester was then cracked by applying a vacuum of 25 mbar and increasing the bottom temperature to 170°–200° C., and the hexenoic acid was distilled off continuously. 291 g of hexenoic acid (boiling point 117° C./25) were obtained, corresponding to a yield of 86.4%, relative to butyraldehyde which had reacted. The absorption of light at 415 nm in a layer of thickness 1 cm was 34%, compared with water.

COMPARISON EXAMPLE 2

(a) The procedure followed was as in part (a) of Comparison Example 1, with the exception that the same quantity of propionaldehyde was employed instead of butyraldehyde.

(b) The procedure followed was analogous to part (b) of Comparison Example 1. 209 g of pentenoic acid (boiling point 107° C./27) were obtained, corresponding to a yield of 60.6%, relative to propionaldehyde which had reacted.

EXAMPLE 2

(a) The procedure followed was as in part (a) of Comparison Example 2.

(b) The procedure followed was analogous to part (b) of Example 1, with the exception that, before the cracking reaction, the mixture, to which water had been added, was heated at 120° C. (under a corresponding excess pressure). 272 g pentenoic acid (boiling point 107° C./27) were obtained, corresponding to a yield of 78.8%, relative to propionaldehyde which had reacted.

COMPARISON EXAMPLE 3

(a) The procedure followed was as in part (a) of Comparison Example 1, with the exception that the same quantity of 2-ethylbutanal was employed instead of butyraldehyde.

(b) The procedure followed was analogous to part (b) of Comparison Example 1. 214 g of 4-ethylhexenoic acid (boiling point 139°–141° C./25) were obtained, corresponding to a yield of 69.3%, relative to ethylbutanal which had reacted.

EXAMPLE 3

(a) The procedure followed was as in part (a) of Comparison Example 3.

(b) The procedure followed was analogous to part (b) of Example 1, with the exception that, before the cracking reaction, the mixture, together with the added water, was boiled under reflux for 50 minutes at 90° C. and under a correspondingly reduced pressure. 260 g of 4-ethylhexenoic acid (boiling point 139°–141° C./25) were obtained, corresponding to a yield of 84.1%, relative to 2-ethylbutanal which had reacted.

COMPARISON EXAMPLE 4

(a) The procedure followed was as in part (a) of Comparison Example 1, with the exception that the same quantity of valeraldehyde was employed instead of butyraldehyde.

(b) The procedure followed was analogous to part (b) of Comparison Example 1. 198 g of heptenoic acid (boiling point 139°–141° C./25) were obtained, corresponding to a yield of 62.6%, relative to valeraldehyde which had reacted.

EXAMPLE 4

(a) The procedure followed was as in part (a) of Comparison Example 4.

(b) The procedure followed was analogous to part (b) of Example 1, with the exception that (before the cracking reaction) the mixture was heated with 50 g of water at 90° C. for 60 minutes. 268 g of heptenoic acid (boiling point 139°–141° C./25) were obtained, corresponding to a yield of 84.8%, relative to valeraldehyde which had reacted.

Comparison Example 5

(a) The procedure followed was as in part (a) of Comparison Example 1, with the exception that the same quantity of i-nonylaldehyde was employed instead of butyraldehyde.

(b) The procedure followed was analogous to part (b) of Comparison Example 1. 174 g of i-undecenoic acid (boiling point 163°–166° C./25) were obtained, corresponding to a yield of 63.2%, relative to i-nonylaldehyde which had reacted.

EXAMPLE 5

(a) The procedure followed was as in part (a) of Comparison Example 5.

(b) The unreacted aldehyde and the toluene were removed by distillation, 40 g of water were added to the residue and the latter was heated to the boil for 30 minutes. The water was then removed by distillation and the residue was subjected to thermal cracking. 219 g of i-undecenoic acid were obtained, corresponding to a yield of 79.5%, relative to i-nonylaldehyde which had reacted.

COMPARISON EXAMPLE 6

(a) Ketene was passed into a mixture of 250 g of methyl ethyl ketone, 250 g of toluene and 2.5 ml of 30% strength boron trifluoride solution in diethyl ether, at 20°–25° C., until the increase in weight corresponded to 80–90% conversion of the ketone employed. After the reaction, 5 g of dimethylstearylamine were added to the mixture containing polyester.

(b) The low-boilers, the unreacted methyl ethyl ketone and the toluene were then removed by distillation. The polyester was then cracked by applying a vacuum of 25 mbar and increasing the bottom temperature to 170°–190° C., and 3-methylpentenoic acid (boiling point 117°–121° C./25) was obtained, corresponding to a yield of 60.1%, relative to methyl ethyl ketone which had reacted.

EXAMPLE 6

(a) The procedure followed was as in part (a) of Comparison Example 6.

(b) The mixture was boiled under reflux with 50 g of water for 60 minutes. The low-boilers, the unreacted methyl ethyl ketone, the water and the toluene were then removed by distillation. The residue was cracked under a vacuum of 25 mbar and at a bottom temperature of 170°–190° C., the 3-methylpentenoic acid (boiling point 117°–121° C./25) being distilled at the same time. 268 g of 3-methylpentenoic acid were obtained, corresponding to a yield of 79.8%, relative to methyl ethyl ketone which had reacted.

We claim:

1. A process for the preparation of of an unsaturated aliphatic carboxylic acid, comprising the following steps in the order named:
    (a) reacting a carbonyl compound with a ketene to form a condensation reaction mixture containing a polyester;
    (b) admixing water with the condensation reaction mixture;
    (c) heating the admixture to a temperature of from 40° C. below the boiling point to the boiling point of the admixture;
    (d) isolating the polyester; and
    (e) thermally cracking the polyester to form the unsaturated aliphatic carboxylic acid.

2. A process as recited in claim 1, wherein the carbonyl compound and the ketene are reacted in contact with a solvent.

3. A process as recited in claim 1, wherein the admixture is heated to a temperature of from 20° C. below the boiling point to the boiling point of the admixture.

4. A process as recited in claim 2, wherein the admixture is heated to a temperature of from 20° C. below the boiling point to the boiling point of the admixture.

5. A process for the preparation of an unsaturated aliphatic carboxylic acid, comprising the following steps in the order named:
    (a) reacting a carbonyl compound with a ketene to form a condensation reaction mixture containing a polyester;
    (b) isolating the polyester from the condensation reaction mixture;
    (c) admixing water with the polyester;
    (d) heating the admixture to a temperature of from 40° C. below the boiling point to the boiling point of the admixture;
    (e) isolating the polyester; and
    (f) thermally cracking the polyester to form the unsaturated aliphatic carboxylic acid.

6. A process as recited in claim 5, wherein the carbonyl compound and the ketene are reacted in contact with a solvent.

7. A process as recited in claim 5, wherein the admixture is heated to a temperature of from 20° C. below the boiling point to the boiling point of the admixture.

8. A process as recited in claim 6, wherein the admixture is heated to a temperature of from 20° C. below the boiling point to the boiling point of the admixture.

* * * * *